United States Patent
Eaton et al.

(10) Patent No.: US 9,795,767 B2
(45) Date of Patent: Oct. 24, 2017

(54) SYSTEMS AND METHODS FOR PERFORMING AN INJECTION

(71) Applicants: Alexander Mellon Eaton, Fort Myers, FL (US); Gabriel Mikal Gordon, Santa Barbara, CA (US); Dyson William Hickingbotham, Wake Forest, NC (US)

(72) Inventors: Alexander Mellon Eaton, Fort Myers, FL (US); Gabriel Mikal Gordon, Santa Barbara, CA (US); Dyson William Hickingbotham, Wake Forest, NC (US)

( * ) Notice: Subject to any disclaimer, the term of this patent is extended or adjusted under 35 U.S.C. 154(b) by 190 days.

(21) Appl. No.: 14/410,567

(22) PCT Filed: Aug. 22, 2013

(86) PCT No.: PCT/US2013/056303
§ 371 (c)(1),
(2) Date: Dec. 22, 2014

(87) PCT Pub. No.: WO2014/031914
PCT Pub. Date: Feb. 27, 2014

(65) Prior Publication Data
US 2015/0148778 A1    May 28, 2015

Related U.S. Application Data

(60) Provisional application No. 61/692,620, filed on Aug. 23, 2012.

(51) Int. Cl.
*A61M 31/00* (2006.01)
*A61M 25/06* (2006.01)
*A61M 5/162* (2006.01)
*A61M 5/32* (2006.01)
*A61M 5/158* (2006.01)

(52) U.S. Cl.
CPC ...... *A61M 25/0612* (2013.01); *A61M 5/1626* (2013.01); *A61M 25/0668* (2013.01); *A61M 5/158* (2013.01); *A61M 5/3216* (2013.01); *A61M 5/3243* (2013.01); *A61M 5/3245* (2013.01); *A61M 2025/0681* (2013.01)

(58) Field of Classification Search
CPC ...... A61M 2025/0681; A61M 25/0612; A61M 25/0668; A61M 5/158; A61M 5/1626; A61M 5/3245
See application file for complete search history.

(56) References Cited

U.S. PATENT DOCUMENTS 3,297,030 A * 1/1967 Czorny .............. A61M 25/0111
                                                 604/160
5,951,518 A * 9/1999 Licata ............... A61M 25/0097
                                                 604/161

* cited by examiner

*Primary Examiner* — Rebecca E Eisenberg
(74) *Attorney, Agent, or Firm* — Ash Tankha; Lipton, Weinberger & Husick

(57) ABSTRACT

Devices, systems, and methods for performing injections with lowered likelihood of infection include catheters and other injection means with protective coverings. The protective covering can protect the catheter or other injection means before, during, or before and during insertion of the catheter into an insertion site. The protective covering includes two or more parts of interlocking protrusions and channels that allow for sliding motion of the parts relative each other but that resist separation of the parts in the direction perpendicular to the long axis of the two or more parts.

7 Claims, 4 Drawing Sheets

SYSTEMS AND METHODS FOR PERFORMING AN INJECTION

CROSS REFERENCE TO RELATED APPLICATIONS

This application is a national phase application of the PCT international application number PCT/US2013/056303 titled "Systems And Methods For Performing An Injection", filed in the United States Patent and Trademark Office as the Receiving Office on 22 Aug. 2013, which claims priority to and the benefit of provisional patent application No. 61/692,620 titled "Systems And Methods For Performing An Injection", filed in the United States Patent and Trademark Office on 23 Aug. 2012.

The specifications of the above referenced patent applications are incorporated herein by reference in their entirety.

TECHNICAL FIELD

Some embodiments of the current subject matter generally relate to the field of injections. In particular, the current subject matter relates to injection devices, systems, and methods configured to prevent or substantially diminish occurrence of an infection during and/or after an injection.

BACKGROUND

Placement of needles for injection or catheters for prolonged infusion of solutions into a patient inherently carries a risk of infection. There are many steps health care givers can take to mitigate infection in terms of sterilization of the injection or infusion site, the instruments, and the health care givers themselves. There is difficulty in protecting a needle or catheter from contamination once it is removed from the cover used in shipping. Protective coverings or sleeves that are known often seek to protect the needles or catheters from contamination as well as protect a user from accidental needle sticks. As such, protective coverings that initially extend over the tip of a needle or catheter before insertion into an injection or infusion site are often configured to return to that position. These types of protective coverings usually require a large extra force to puncture an injection or infusion site, which is undesirable when dealing with sensitive areas of the human body or with sensitive patients.

SUMMARY

In some embodiments, the current subject matter relates to a system for performing an injection at an injection site. The system includes an injection device having an injection needle configured to penetrate the injection site and a sleeve configured to house the injection needle, wherein the sleeve is configured to cover the injection needle at least partially before and during the injection without penetrating the injection site.

In some embodiments, an apparatus includes an infusion system and a protective covering that can include two interacting parts. The infusion system can include a needle or a catheter and a hub. The two interacting parts of the protective covering can include a first protective part and a second protective part which create a channel between the two interacting parts. The channel can be such that it surrounds the needle or catheter before and during an injection.

In some embodiments, an apparatus can additionally include any or all of the following features. The first protective part can include two or more protrusions and the second protective part can include two or more channels into which the protrusions fit. In some embodiments of the apparatus, the effective diameter of the channel between the two interacting parts can be less than the diameter of the hub.

In some embodiments, a method includes advancing an infusion system assembly that includes a needle or a catheter and a hub towards an infusion site while a protective covering surrounds the needle or catheter, in which the protective covering includes two or more parts that interact to form a channel through which the needle or catheter fits. The method further includes separating the two or more parts of the protective covering as the hub advances through the protective covering and removing the protective covering after the needle or catheter is fully inserted into an infusion site.

In some embodiments, a method can additionally include any or all of the following features. In some embodiments, removing the protective covering can include allowing the two or more parts of the protective covering to fall away from each other. Additionally, in some embodiments, removing the protective covering includes actively removing the two or more parts of the protective covering from the infusion system assembly.

BRIEF DESCRIPTION OF THE DRAWINGS

The current subject matter is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

As stated above, some embodiments of the current subject matter relate to injection or infusion devices, systems, and/or methods configured to prevent and/or substantially reduce occurrence of an infection during and/or after the injection or infusion. The device, systems, and methods described herein allow for injections or infusions in a manner that reduces the likelihood of infection, while possibly reducing the added force when using an injection or infusion system with a protective covering.

The needles used in the devices, systems, and methods described herein are generally made of metals, such as stainless steel (303, 304, 316, or 400 series (e.g. 420)), titanium, or such other metals or alloys, but can also be made out of plastic, glass or ceramic materials depending on the application. The catheters used in the devices, systems, and methods described herein generally include a metal or hard polymer insertion needle or wire and a polymer catheter tube. The catheter tube may be any suitable material that is biocompatible, such as a material that will not cause thrombosis or irritation at the insertion site.

In some embodiments, a protective covering may be used to cover a metal or plastic needle that is used to inject fluids, medications or other materials into IV tubing, butterfly needles, parenteral nutrition tubing, respiratory tubing, urinary, cerebral spinal fluid or any other medical tubing used to deliver fluids or materials to human or animals. A protective cover can also be used to cover catheters that are used for intravenous, intra-arterial, abdominal, renal, central nervous system or any other access.

Figure 1:
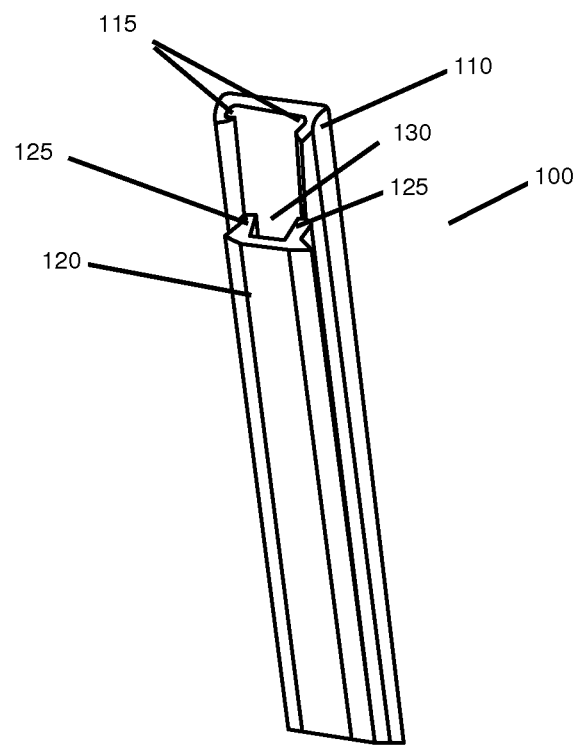
FIG. 1 illustrates an exemplary cover for an intravenous catheter or injection system.

FIG. 1 illustrates an exemplary protective covering 100 that can be used with a needle or a catheter before and during insertion into an injection or infusion site. The protective covering 100 includes two parts, a channel portion of the cover 110 and a protrusion portion of the cover 120. The two parts 110 and 120 of the protective covering 100 interact such that the channels 115 in the channel portion 110 receive the protrusions 125 on the protrusion portion 120. The materials of and design of the channels 115 and protrusions 125 allow them to deform and allow the protective covering 100 to form a channel 130 through the length of the protective covering 100. The channel 130 can receive a needle or a catheter. The channel portion 110 slideably engages and interlocks with the protrusion portion 120.

The protective covering 100 can be a plastic material. The protrusion portion 120 can be a different material than the channel portion 110. The protrusions 125 can be a different material than the portions of the protrusion portion 120 that do not interlock with the channels 115. The protrusions 125 can be an elastomeric material, such as silicone. The protective covering 100 can be formed through an extrusion process, an injection molding process, or any other suitable polymer formation process. The channel 130 can be uniform in dimension across the length of the protective covering 100. Alternatively, the channel 130 can taper in depth, width, or both depth and width across the length of the protective covering 100. The two parts 110 and 120 of the protective covering 100 can be the same length or different lengths. In some embodiments, the lengths of the two parts 110 and 120 of the protective covering 100 can differ by 10% or less of the length of the longer part.

Figure 2A:
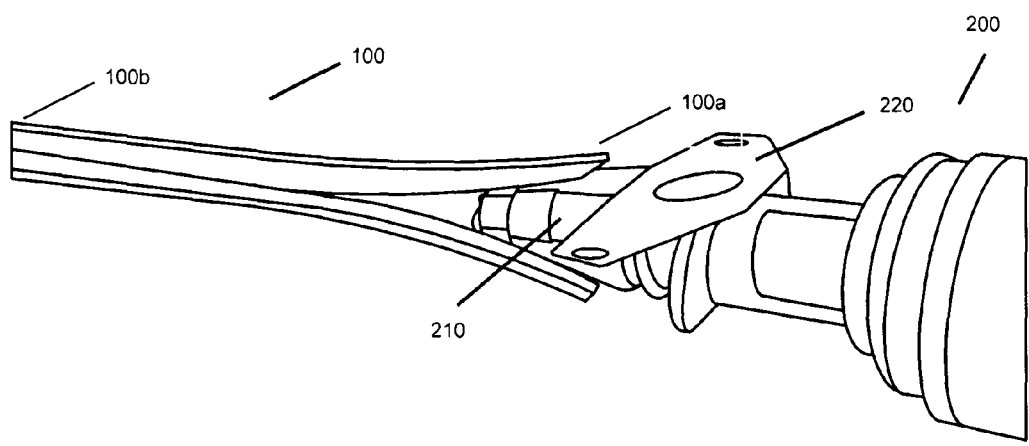
FIG. 2A illustrates a catheter insertion system with a protective cover.
Figure 2B:
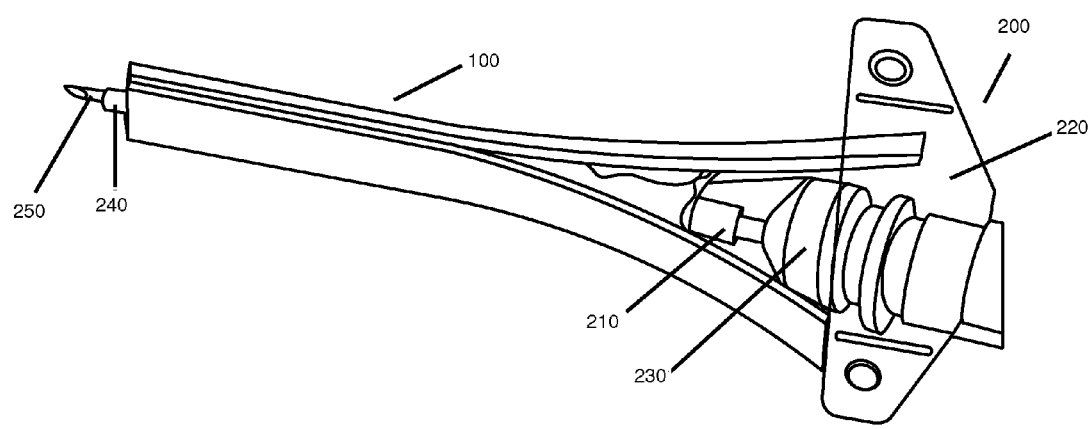
FIG. 2B illustrates another view of a catheter insertion system with a protective cover.

FIG. 2A shows a catheter insertion assembly 200 inserted into a protective covering 100. The catheter insertion assembly 200 has a catheter tube which at its proximal end 210 is connected to a hub and a winged portion 220. The catheter tube fits into the channel 130 in FIG. 1. As shown, the catheter insertion assembly 200 has just been inserted into the protective covering 100 or is in a pre-insertion configuration. More specifically, a distal end 240 of the catheter insertion assembly 200 having a needle 250 is inserted into a top end 100*a* of the protective covering 100. Moreover, when the needle 250 is fully inserted into the protective covering 100, the channel portion 110 and the protrusion portion 120 are split along the length of the protective covering 100 and the needle 250 protrudes out of a bottom end 100*b* of the protective covering 100 as shown in FIGS. 2A-2B. The proximal end 210 of the catheter tube is located near one extremity of the protective covering 100. The winged portion 220 can be used to help position the catheter into an infusion site as well as to affix the catheter assembly to a patient in the manner known in the medical arts. In use, the winged portion 220 is near a patient's skin when the catheter tube in inserted in an infusion site.

FIG. 2B shows a view of a catheter insertion assembly 200 as the assembly 200 is being inserted into in an infusion site. This view of the catheter insertion assembly 200 shows the distal end 240 of the catheter tube with an insertion needle 250 protruding from it. The majority of the catheter tube is surrounded by the protective covering 100. The proximal end 210 of the catheter tube can be seen adjacent to the catheter hub 230. The catheter hub 230 is adjacent to the winged portion 220 which is located near portions of the protective covering 100 that have separated. The protective covering 100 has split to allow the catheter insertion assembly 200 to progress further down the channel (130 in FIG. 1).

Figure 3:
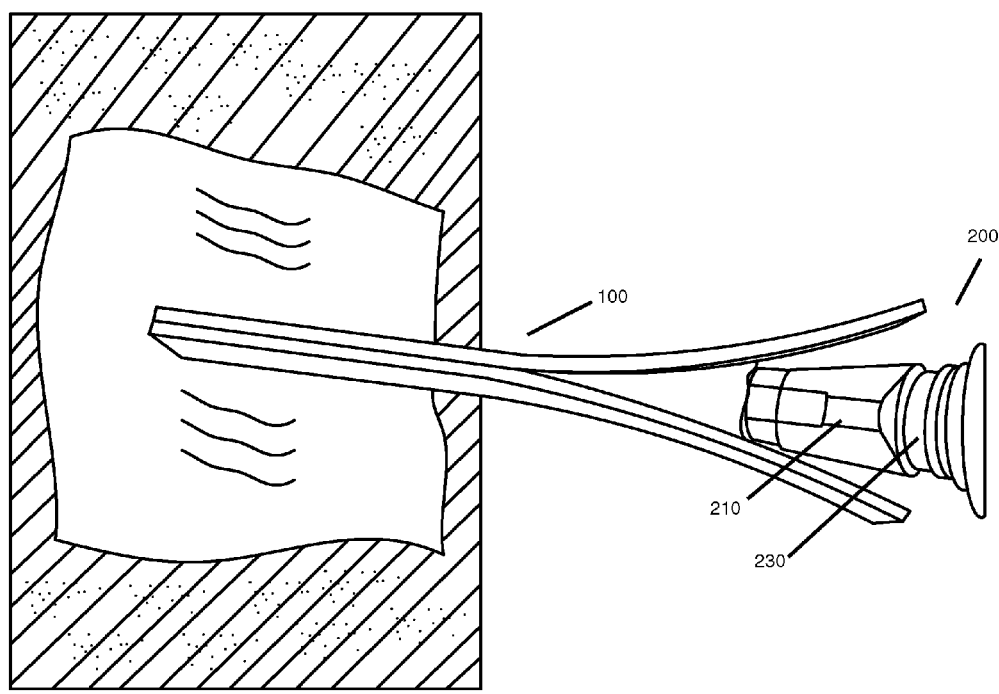
FIG. 3 illustrates a catheter insertion system with a protective cover in which the distal end of the catheter insertion system is pressing against the surface of an insertion site.

FIG. 3 illustrates another view of a catheter insertion assembly 200 with a protective covering 100 being inserted into an infusion site. The distal end (240 in FIG. 2B) of the catheter tube is not shown in this view because it is beneath the surface of the infusion site. The winged portion (220 in FIG. 2B) is also not shown in this view because of the angle of the catheter insertion assembly 200. In this view, the proximal end 210 of the catheter tube is more easily seen as it approaches the middle of the protective covering 100. As the catheter insertion assembly 200 is more fully inserted into the infusion site, the protective covering 100 is further split. Once the catheter is fully inserted, the protective covering 100 can come fully apart and separate from the catheter insertion assembly or a user can remove the protective covering 100.

The protrusion portion 120 and the channel portion 110 of the protective covering 100 can slide relative to each other. For example, if the protrusion portion 120 is held in place and a force is exerted on the channel portion 110 along the longitudinal axis of the channel portion 110, the channel portion 110 will slide. Conversely, the protrusion portion 120 and the channel portion 110 of the protective covering 100 do not easily separate in any direction off the longitudinal axis. The channel 130 is smaller in effective cross-section than the cross section of hub 230, such that as the hub 230 travels along the length of the protective covering 100, the protrusion portion 120 and the channel portion 110 separate. The size of the channel 130 relative to the size of the hub 230 can be chosen so that as the hub 230 approaches the surface of the infusion site, the parts of the protective covering 100 will fall apart.

A protective covering that falls apart after insertion of the needle or catheter into an injection or infusion site can avoid contamination of the site by the protective covering. The protective covering described herein can avoid the possibility of folding in on itself and contaminating the catheter or needle. The protective covering can also be coordinated with the size of the needle or catheter hub of the injection or infusion assembly to influence the amount of force needed to separate the pieces of the protective covering. In this way, an injection or infusion insertion assembly can be used with a protective covering in a delicate area or with a sensitive patient without causing a large amount force to be applied to the injection or infusion site.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the claims.

We claim:

1. An apparatus comprising:
   an infusion system comprising a needle or a catheter and a hub; and
   a protective covering, the protective covering comprising a channel portion and a protrusion portion, wherein the channel portion extends through a length of the protective covering, wherein the channel portion slideably engages and interlocks with the protrusion portion, wherein the channel portion is configured to receive the needle or the catheter from a top end of the protective covering, wherein the protective covering is configured to surround and cover the needle or the catheter before and during an injection, and wherein the channel portion and the protrusion portion are configured to split from each other to allow the needle or the catheter to progress further down the length of the protective covering during the injection.

2. The apparatus of claim 1, wherein the protrusion portion comprises two or more protrusions and the channel portion comprises two or more channels into which the protrusions fit, and wherein the channel portion is smaller in effective cross-section than cross-section of the hub, wherein the hub travels along the length of the protective covering thereby splitting the protrusion portion and the channel portion.

3. A method of advancing an infusion system assembly comprising a needle or a catheter and a hub towards an infusion site while a protective covering surrounds the needle or the catheter before and during an injection, the method comprising:
   providing the protective covering comprising a protrusion portion and a channel portion, wherein the protrusion portion slidably engages and interacts with the protrusion portion, wherein the channel portion extends through a length of the protective covering;
   inserting the needle or the catheter of the infusion system assembly into the protective covering from a top end of the protective covering, wherein the channel portion receives the needle or the catheter from the top end of the protective covering;
   injecting the needle or the catheter into the infusion site;
   advancing the needle or the catheter into the infusion site, wherein the hub of the infusion system assembly travels along the length of the protective covering and splits the channel portion and the protrusion portion from each other; and
   removing the protective covering after the needle or the catheter is fully inserted into the infusion site.

4. The method of claim 3, wherein removal of the protective covering comprises allowing the channel portion and the protrusion portion to fall away from each other.

5. The method of claim 3, wherein removal of the protective covering comprises actively removing the channel portion and the protrusion portion from the infusion system assembly.

6. An apparatus comprising:
   an infusion system comprising a needle or a catheter and a hub; and
   a protective covering comprising two interacting parts, the interacting parts comprising a first protective part and a second protective part, wherein the first protective part and the second protective part are disposed to form a channel between the first protective part and the second protective part, wherein the channel tapers in one or more of depth and width across a length of the protective covering, wherein the channel is configured to surround and cover the needle or the catheter before and during an injection, wherein one of the two interactive parts is substantially shorter in length than other interactive part, and wherein the two interactive parts are configured to split from each other to allow the needle or the catheter to progress further down the length of the protective covering during the injection.

7. The apparatus of claim 6, wherein a length of the one of the two interactive parts differs by ten percent or less than a length of the other interactive part.

* * * * *